(12) United States Patent
Maruta et al.

(10) Patent No.: US 8,083,903 B2
(45) Date of Patent: Dec. 27, 2011

(54) PROCESS FOR PRODUCING ALLYL ALCOHOL

(75) Inventors: Hiroshi Maruta, Oita (JP); Chihiro Otogawa, Oita (JP)

(73) Assignee: Showa Denko K.K., Tokyo (JP)

( * ) Notice: Subject to any disclaimer, the term of this patent is extended or adjusted under 35 U.S.C. 154(b) by 675 days.

(21) Appl. No.: 12/162,027

(22) PCT Filed: Feb. 1, 2007

(86) PCT No.: PCT/JP2007/052169
§ 371 (c)(1),
(2), (4) Date: Jul. 24, 2008

(87) PCT Pub. No.: WO2007/089036
PCT Pub. Date: Aug. 9, 2007

(65) Prior Publication Data
US 2009/0166174 A1 Jul. 2, 2009

(30) Foreign Application Priority Data
Feb. 2, 2006 (JP) ................. 2006-026051

(51) Int. Cl.
B01D 3/34 (2006.01)
B01D 3/10 (2006.01)
B01D 3/00 (2006.01)

(52) U.S. Cl. ................. 203/60; 203/29; 203/38; 203/82; 203/84

(58) Field of Classification Search ............. 203/29, 203/38, 63, 71, 74, 84, 60, 82
See application file for complete search history.

(56) References Cited

U.S. PATENT DOCUMENTS 2,485,694 A * 10/1949 Burchfield .............. 203/82
3,970,713 A * 7/1976 Scharfe et al. ........... 568/877

FOREIGN PATENT DOCUMENTS

| | | |
|---|---|---|
| GB | 1 298 929 A | 12/1972 |
| JP | 60-237032 A | 11/1985 |
| JP | 62-149637 A | 7/1987 |
| JP | 62-149638 A | 7/1987 |
| JP | 64-85940 A | 3/1989 |
| JP | 4-235138 A | 8/1992 |
| JP | 7-25796 A | 1/1995 |
| SU | 373934 | 9/1973 |
| TW | 442462 | 6/2001 |
| WO | 97/29068 A1 | 8/1997 |

* cited by examiner

Primary Examiner — Glenn Caldarola
Assistant Examiner — Patrick McCarty
(74) Attorney, Agent, or Firm — Sughrue Mion, PLLC

(57) ABSTRACT

An azeotropic distillation method, comprising a reaction step, a distillation step for separating and refining a reaction product, and a recovery step for collecting a reactant after the distillation step; wherein at least one component constituting the reactant in the reaction step can act as an entrainer for the azeotropic distillation in the distillation step; and a portion of the reactant capable of acting as the entrainer is supplied to the distillation step.

2 Claims, 4 Drawing Sheets

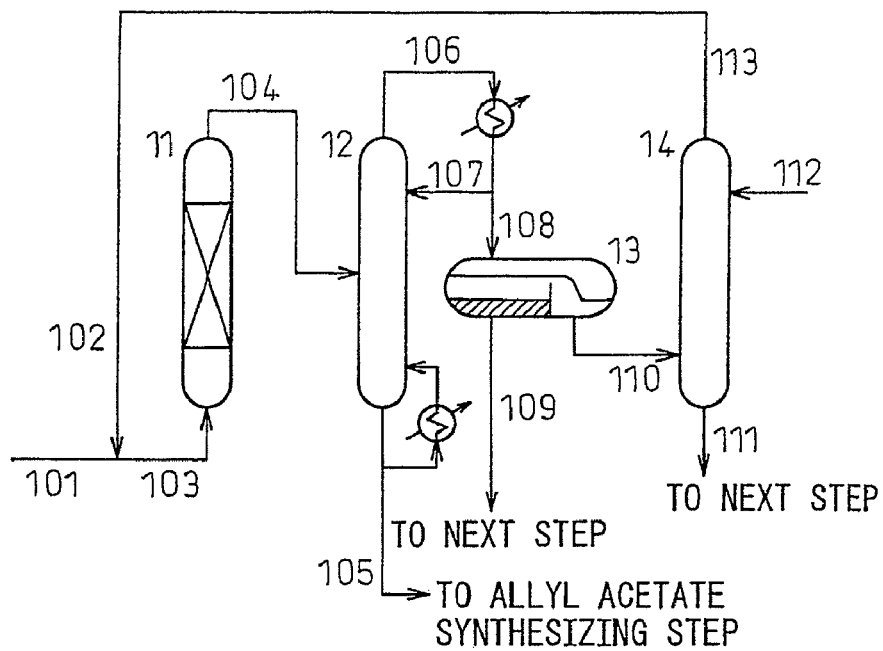
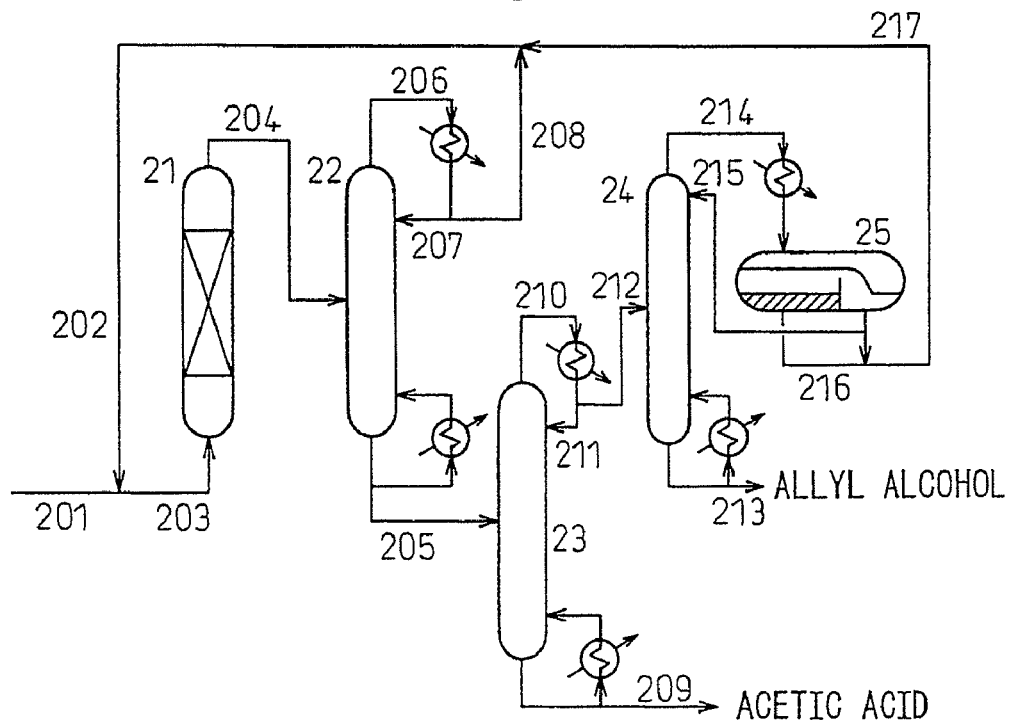

PRIOR ART Fig.3
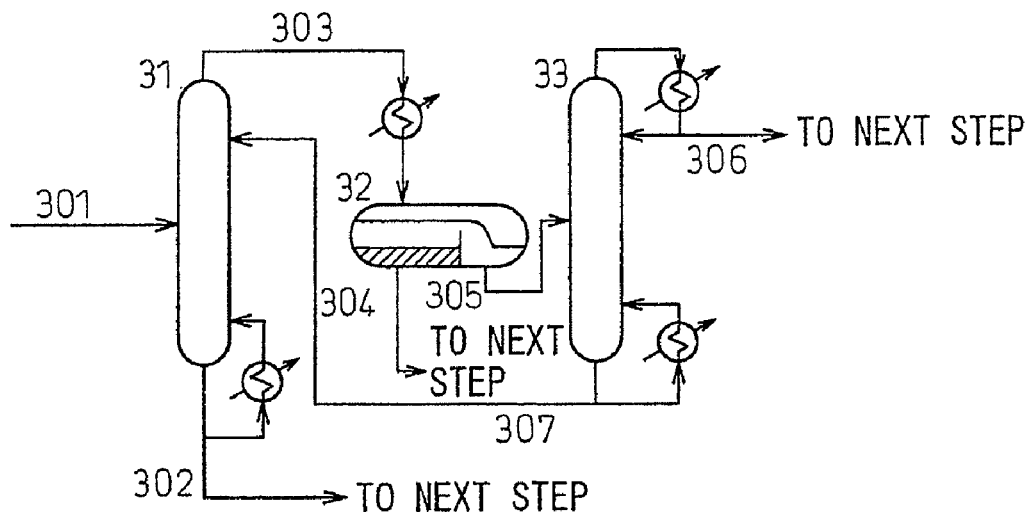
Fig.4
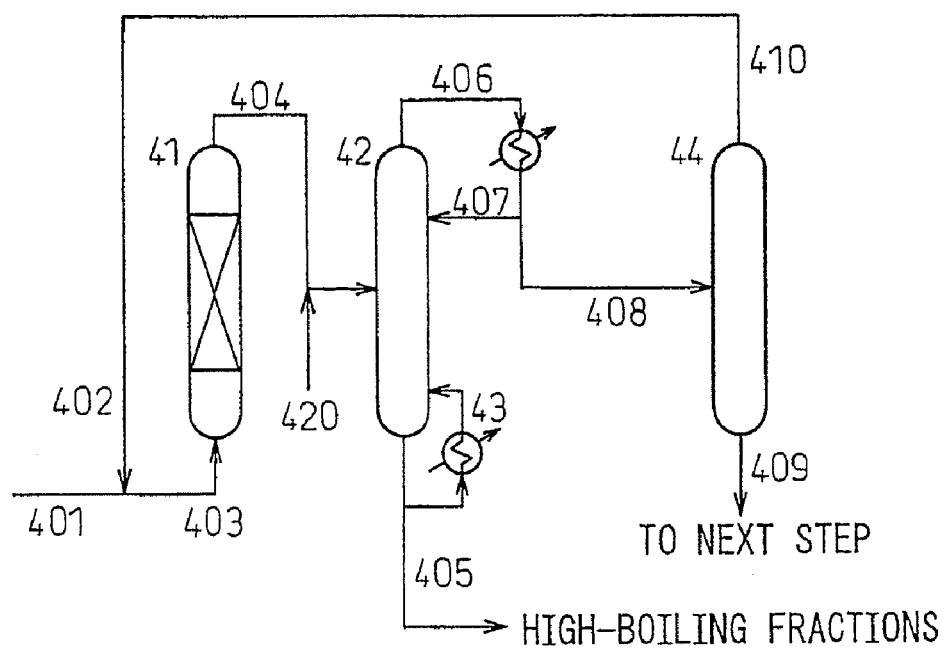

1

PROCESS FOR PRODUCING ALLYL ALCOHOL

TECHNICAL FIELD

The present invention relates to an azeotropic distillation method. More specifically, the present invention relates to an azeotropic distillation method comprising a reaction step and a distillation step for separating and refining (or purifying) reaction product(s), wherein a portion of the reactant is supplied to the distillation step so as to improve the separation performance of the azeotropic distillation, in a system in which a reactant (or raw material for reaction) acts as an entrainer (or auxiliary agent) for the azeotropic distillation in the distillation step, whereby the energy required for the separation may be reduced.

BACKGROUND ART

An azeotropic phenomenon takes place in a combination of two or more components which may provide a maximum azeotropic point or a minimum azeotropic point. In an "azeotropic distillation" utilizing the azeotropic phenomenon, when a substance (generally called an "entrainer" or "auxiliary agent") capable of forming an azeotropic mixture with at least one of any of at least two substances, which are difficult to be separated from each other by simple distillation or fractional distillation, is added to the mixture comprising the above-mentioned at least two substances, the separation performance of the distillation may be improved. Examples of the industrial fields in which the azeotropic distillation is applicable, may include: a step for producing allyl alcohols through the hydrolysis reaction of allyl acetate (Patent Document 1 and Patent Document 2), or a step for purifying 2,3-dichloro-1-propanol (Patent Document 3).

Patent Document 1 discloses a method for collecting allyl acetate from an azeotropic mixture comprising allyl acetate (which is one reactant component for a hydrolysis reaction), water, and allyl alcohol (which is a reaction product), through an extraction operation. However, in this Patent Document 1, all of the amount of the collected allyl acetate is supplied to the reaction step, and Patent Document 1 does not teach or suggest an effect of supplying the allyl acetate as an entrainer to a distillation column.

Patent Document 2 discloses an azeotropic distillation method, wherein allyl acetate, which is one reactant component of a hydrolysis reaction, is used as an azeotropic entrainer for water separation. However, in the same manner as in Patent Document 1, Patent Document 2 does not teach or suggest an effect of supplying the allyl acetate as an entrainer to a distillation column.

On the other hand, Patent Document 3 discloses an azeotropic distillation method, wherein a by-product of the reaction is concentrated and the resultant concentrate is used as an entrainer. However, in this Patent Document 3, the entrainer used is not a reactant, and therefore the entrainer is not recycled to the reaction step.

Hereinbelow, each the Patent Documents is described in more detail.

FIG. 1 is a flow diagram for illustrating the process of Patent Document 1. Referring to FIG. 1, in such a process, a reactant (103) which comprises a reactant (101) mainly comprising allyl acetate and water, and a collected (or recycled) allyl acetate (102) which has been mixed with the reactant (101), is introduced into a hydrolysis reactor (11). A reaction product liquid (104) which has been taken out from the hydrolysis reactor (11) is introduced into the first distillation column (12), and is subjected to distillation therein, and the bottom liquid (105) including aqueous acetic acid, etc., is discharged from the distillation column, and the discharged liquid is recycled into the allyl acetate producing step.

On the other hand, a distilled azeotropic mixture (106) comprising allyl alcohol, allyl acetate and water is discharged from the top of the first distillation column (12), and is introduced into a decanter (13). In the decanter, the above-mentioned mixture (106) is separated into two layers: an oil layer (110) which is rich in allyl acetate, and an aqueous layer (109) which is poor in allyl acetate. The oil layer (110) is introduced to an extraction tower (14). In this extraction tower (14), the allyl acetate is removed by means of an extraction operation using an extraction agent (112) mainly comprising water. The bottom liquid (111) mainly comprising allyl alcohol and water, and the bottom liquid is refined to allyl alcohol including a slight amount of water in a post-process distillation operation. On the other hand, a liquid (113) comprising water and allyl acetate containing substantially no allyl alcohol is taken out from the top of the extraction column (14), and is supplied to the reactor (11) as the above-mentioned recycled liquid (102).

FIG. 2 is a flow diagram for illustrating the process of Patent Document 2. Referring to FIG. 2, a reactant liquid (201) mainly comprising allyl acetate and water, a recycled liquid (202) comprising allyl acetate as a recycled reactant component and water are passed, in combination, through a hydrolysis reactor (21) so as to cause a hydrolysis reaction of allyl acetate, to thereby obtain allyl alcohol and acetic acid. The reaction product liquid (204) produced by the reactor (21) comprises allyl acetate, allyl alcohol, water and acetic acid, and is supplied to the first distillation column (22). A portion of unreacted allyl acetate is collected from the top of the first distillation column (22) as an azeotropic mixture of allyl acetate, water and allyl alcohol, and a distillate liquid (208) is recycled to the above-mentioned hydrolysis reactor (21).

On the other hand, the thus produced acetic acid, allyl alcohol, the unreacted water, and a portion of the unreacted allyl acetate are taken out from the bottom of the first distillation column (22). The liquid (205) taken out from the bottom of the first distillation column (22) is supplied to the second distillation column (23). By use of the allyl acetate in the liquid (205) as an azeotropic entrainer, an azeotropic mixture liquid (212) of allyl alcohol, water and allyl acetate is obtained from the top of the column, and a liquid (209) mainly comprising acetic acid, or acetic acid and water is obtained from the bottom of the column. The fraction of distillate (212) at the column top of the second distillation column (23) is supplied to the third distillation column (24).

Water, allyl acetate and allyl alcohol are discharged from the top of the third distillation column (24), and after the condensation of such a mixture, the mixture is separated into two layers (namely, an oil layer and an aqueous layer) in a decanter (25). The oil layer mainly comprises allyl acetate. A portion or all of this organic phase is recycled to the column (24) as an azeotropic entrainer so as to purify the allyl alcohol. The aqueous layer contains small amounts of allyl alcohol and allyl acetate and is returned to the hydrolysis reactor (21) together with a portion of the above-mentioned oil layer.

FIG. 3 is a flow diagram for illustrating the process of Patent Document 3. Referring to FIG. 3, a liquid (301) in this process mainly comprising an intermediate product (namely, 2,3-dichloro-1-propanol (hereinafter, referred to as "DCH")) to be produced in an epichlorohydrin-producing process using allyl alcohol as a reactant, and also contains 1,2,3-trichloropropane (hereinafter, referred to as "TCP") as a by product, and other low-boiling point substances. The liquid (301) is supplied to a first distillation column (31), and a liquid (307) mainly comprising TCP is supplied from the top of the first distillation column (31) as an entrainer. Because of the presence of the TCP supplied from the top of the column which acts as an entrainer, the water in the liquid (301) is formed into a TCP-water azeotropic mixture having a boiling point which is lower than that of a DCH-water azeotropic mixture, is subjected to distillation and moved toward the top of the column, so as to provide a column-top distillate (303) from the first distillation column (31). Consequently, a large portion of the water is formed into the TCP-water azeotropic mixture in the distillation, and therefore the production of distilled DCH at the top of the column is suppressed. The liquid (302) at the bottom of the column is supplied to the refining equipment to be used in a subsequent process. The column-top distillate (303) is condensed, cooled and is separated into an aqueous layer (304) and an oil layer (305) in a decanter (32). The aqueous layer (304) is supplied to a separately provided processing equipment. The oil layer (305) is supplied to the second distillation column (33), and supplied from the bottom of the column to the first distillation column (31) as a liquid (307) mainly comprising TCP. The column-top distillate (306) is introduced to a separately provided processing equipment.

In recent years, in view the need for reduction in carbon dioxide emissions and for fuel saving, there are intense demands for the reduction in the energy to be required for the separation in azeotropic distillation without substantively decreasing the separation performance therein.

[Patent Document 1] JP-A (Japanese Unexamined Patent Publication; Kokai) No. 62-149637
[Patent Document 2] JP-A No. 1-85940
[Patent Document 3] JP-A No. 7-25796

DISCLOSURE OF INVENTION

An object of the present invention is to provide an azeotropic distillation method which is capable of reducing the energy required for the separation in azeotropic distillation without substantively decreasing the separation performance therein.

As a result of earnest study, the present inventors have found that, when a portion of a reactant component in a reaction step is supplied to a distillation step so as to positively use the portion of the reactant as an (azeotropic entrainer, the separating performance of the distillation step with respect to the reactant in the reaction step may rather be improved, whereby the overall or total energy consumption can be reduced.

The azeotropic distillation method according to the present invention is based on the above-mentioned discovery. More specifically, the azeotropic distillation method according to the present invention comprises: at least, a reaction step, a distillation step for separating and refining (or purifying) a reaction product, and a recovery step for collecting a reactant after the distillation step; wherein at least one component constituting the reactant in the reaction step can act as an entrainer for the azeotropic distillation in the distillation step; and a portion of the reactant capable of acting as the entrainer is supplied to the distillation step.

In the azeotropic distillation method according to the present invention having the above-mentioned constitution, it is possible to obtain an advantage that the separation performance in the azeotropic distillation can be improved by supplying a portion of the reactant to the distillation step as an azeotropic distillation entrainer. In such a case, an increase in the amount of unreacted reactant to be recycled or circulated could be a cause of disadvantage, but the present inventors have found that such a disadvantage is substantially negligible, because of a reduction in the mixing of high boiling point component(s) into the distillate liquid, a reduction in the load of water drainage, etc., in the present invention.

In the present invention, in a case where a reactant acts also as an azeotropic entrainer, the separation performance of the distillation step can be raised by supplying at least a portion of the reactant to the distillation step (without supplying portion of the reactant to the reaction system) as an azeotropic entrainer, whereby the energy required for the distillation step can be reduced.

The present invention may include, for example, the following embodiments [1] to [4].

[1] An azeotropic distillation method, comprising at least, a reaction step, a distillation step for separating and refining a reaction product, and a recovery step for collecting a reactant after the distillation step;
wherein at least one component constituting the reactant in the reaction step can act as an entrainer for the azeotropic distillation in the distillation step; and a portion of the reactant capable of acting as the entrainer is supplied to the distillation step.

[2] The azeotropic distillation method according to [1], wherein a portion of the liquid and/or gas, which has been recovered in a post-step after the distillation step, and comprises 80 mass % or more of the unreacted reactant which acts as an entrainer, is supplied to the distillation step.

[3] The azeotropic distillation method according to [2], wherein the distillation step uses a plurality of distillation columns, and a portion of the liquid and/or gas comprising 80 mass % or more of the unreacted reactant which acts as an entrainer, is supplied to the first column to be used in the distillation step.

[4] The azeotropic distillation method according to any of [1] to [3], wherein the reactant acting as the entrainer is allyl acetate, and the reaction product comprises allyl alcohol and acetic acid.

[5] A process for producing allyl alcohol, including the azeotropic distillation method according to [4], as a part of the process.

As described above, according to the present invention, the separation performance in the azeotropic distillation can be improved, and as a result, the energy consumption in the distillation step can be reduced, and the concentration of a high-boiling point component in the fraction of distillate at the top of the column to be used in the distillation step can be reduced.

BRIEF DESCRIPTION OF DRAWINGS

FIG. 1 is a flow diagram for illustrating the process flow of Patent Document 1.
FIG. 2 is a flow diagram for illustrating the process flow of Patent Document 2.
FIG. 3 is a flow diagram for illustrating the process flow of Patent Document 3.
FIG. 4 is a flow diagram for illustrating the process flow of an embodiment of the present invention.

EXPLANATION OF REFERENCE NUMERALS

Figure 5:
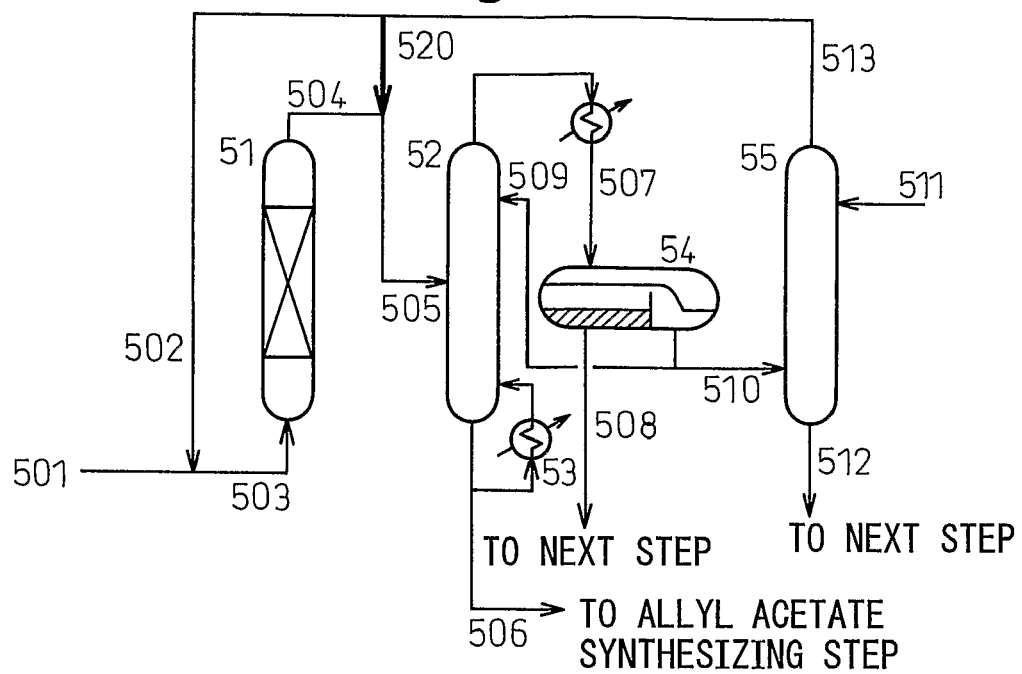
FIG. 5 is a flow diagram for illustrating the process flow of Examples 1 and 3.

11: hydrolysis reactor
12: distillation column
13: decanter
14: extraction column
21: hydrolysis reactor
22: first distillation column
23: second distillation column
24: third distillation column
25: decanter
31: first distillation column
32: decanter
33: second distillation column
41: reaction step
42: azeotropic distillation column
43: reboiler for azeotropic distillation column (42)
44: reactant recovery step
51: hydrolysis reactor
52: azeotropic distillation column
53: reboiler for azeotropic distillation column (52)
54: decanter
55: extraction column
101: hydrolysis reactant liquid
102: collected reactant liquid
103: liquid to be supplied to hydrolysis reactor (11)
104: reaction product liquid of hydrolysis reactor (11)
105: column-bottom discharged liquid of first distillation column (12)
106: column-top vapor of the first distillation column (12)
107: circulating liquid of the first distillation column (12)
108: discharged oil-layer liquid of the decanter (13)
109: discharged aqueous-layer liquid of the decanter (13).
110: water extract of the extraction column (14)
111: liquid extract of the extraction column (14)
112: liquid remaining after extraction in the extraction column (14)
201: hydrolysis reactant liquid
202: collected reactant liquid
203: liquid to be supplied to the hydrolysis reactor (21)
204: reaction product liquid of the hydrolysis reactor (21)
205: column-bottom discharged liquid of the first distillation column (22)
206: column-top vapor of the first distillation column (22)
207: reflux of the first distillation column (22)
208: liquid distillate of the first distillation column (22)
209: column-bottom discharged liquid of the second distillation column (23)
210: column-top vapor of the second distillation column (23)
211: circulating liquid of the second distillation column (23)
212: liquid distillate of the second distillation column (23)
213: column-bottom discharged liquid of the third distillation column (24)
214: column-top vapor of the third distillation column (24)
215: reflux of the third distillation column (24)
216: discharged aqueous-layer liquid of the decanter (25)
217: discharged oil-layer liquid of the decanter (26)
301: feed liquid of the first distillation column (31)
302: column-bottom discharged liquid of the first distillation column (31)
303: column-top vapor of the first distillation column (31)
304: discharged aqueous-layer liquid of the decanter (32)
305: discharged oil-layer liquid of the decanter (32)
306: liquid distillate of the second distillation column (33)
307: entrainer liquid collected from the second distillation column (33)
401: reactant liquid
402: unreacted reactant liquid collected
403: liquid to be supplied to the reaction step (41)
404: reaction product liquid of the reaction step (41)
405: column-bottom discharged liquid of the azeotropic distillation column (42)
406: column-top vapor of the azeotropic distillation column (42)
407: circulating liquid of the azeotropic distillation column (42)
408: liquid distillate of the azeotropic distillation column (42)
409: liquid remaining after the unreacted reactant is collected from the reactant recovery step (44)
410: unreacted reactant liquid collected from the reactant recovery step (44)
420: reactant liquid supplied as an entrainer to the azeotropic distillation column (42)
501: hydrolysis reactant liquid
502: reactant liquid collected
503: liquid to be supplied to the hydrolysis reactor (51)
504: reaction product liquid of the hydrolysis reactor (51)
505: feed liquid of the azeotropic distillation column (52)
506: column-bottom discharged liquid of the azeotropic distillation column (52)
507: column-top vapor of the azeotropic distillation column (52)
508: discharged aqueous-layer liquid of the decanter (54)
509: circulating liquid of the azeotropic distillation column (52)
510: discharged oil-layer liquid of the decanter (54)
511: water extract of the extraction column (55)
512: liquid extract of the extraction column (55)
513: liquid remaining after extraction in the extraction column (55)
514: acetic acid collected from high-boiling waste liquid
515: allyl acetate collected from next step
520: collected reactant liquid added to the reaction product liquid (504) of (51)
521: collected reactant liquid added to the reflux (509) of the azeotropic distillation column (52)

BEST MODE FOR CARRYING OUT THE INVENTION

Hereinbelow, the present invention will be described in detail, with reference to the accompanying drawings as desired.

Azeotropic Distillation Method

The azeotropic distillation method according to the present invention comprises a reaction step and a distillation step for separating and refining (or purifying) reaction product(s). In the present invention, a portion of the reactant is supplied to the distillation step so as to improve the separation performance of the azeotropic distillation, in a system in which a reactant (or raw material for reaction) acts as an entrainer (or auxiliary agent) for the azeotropic distillation in the distillation step.

Azeotropy

In a combination (i.e., azeotropic mixture) of at least two components which provide a maximum azeotropic point or a minimum azeotropic point (hereinafter, these maximum and minimum azeotropic points are collectively referred to as "azeotropic point"), an azeotropic phenomenon occurs. At an azeotropic point, the composition of a vapor to be generated from a liquid becomes equal to the composition of the liquid. In the present invention, azeotropic distillation is conducted by utilizing such an azeotropic phenomenon.

Combination Providing Azeotropic Mixture

The combination of components for providing an azeotropic mixture is not specifically limited in the present invention, as long as the combination provides a system wherein at least one component constituting a reactant acts as an azeotropic distillation entrainer in a distillation step. For example, in the present invention, the following combination may suitably be used.

(1) Water-allyl Acetate-allyl Alcohol

Entrainer

In the present invention, the "entrainer" (also referred to in some cases as an "azeotropic agent") refers to a component such that, when the component is added to a mixture comprising two or more substances, which are less liable to be separated from each other by simple distillation or fractional distillation, provided that the component can form an azeotropic mixture with at least one of the two or more substances, the separation performance of the distillation may be improved. In the present invention, at least one component constituting the reactant acts as an azeotropic distillation entrainer in the distillation step. The criterion for judging whether a certain component will act as an entrainer, is determined by whether or not the addition of any of the component for providing an azeotropy causes the resultant azeotropic point to move close to the composition providing the maximum azeotropic point or the minimum azeotropic point.

An Embodiment of the Present Invention

FIG. 4 is a flow diagram showing an embodiment of the present invention. Referring to FIG. 4, a liquid (401) containing a reactant flows to join with a circulating liquid (402) comprising a reactant recovered from a reactant recovery step (44) appearing hereinafter, and the resultant liquid mixture is supplied as a reactant (403) to a reaction step (41). A reaction product liquid (404) discharged from the reaction step (41) flows to join with flow (420) including reactant which acts as an entrainer, and the resultant liquid mixture is supplied to an azeotropic distillation column (42).

A column-bottom liquid (405) comprising mainly a high boiling component is taken out from the reaction product liquid (404) that is supplied to the azeotropic distillation column (42) via the bottom of the column by means of a distillation operation, and a column-top fraction of distillate (406) comprising an azeotropic mixture containing an entrainer is taken out via the top of the column. A portion of the column-top fraction of distillate (406) is returned to the azeotropic distillation column (42) as a reflux (407), and the remaining liquid (408) is supplied to the reactant recovery step (44). In the reactant recovery step (44), an any separating operation can be used, in addition to the distillation and extraction, as long as a reactant can be collected. The specific separating operation to be used may be determined on the basis of criteria such as costs required for collecting the raw material or the recovery rate of the collection. A reactant (410) collected from the reactant recovery step (44) is supplied to the reaction step (41) as the reactant (402).

Incidentally, the position where the flow (420) including the reactant is added is not limited to the position of that of the reaction product liquid (404). For example, the flow (420) including the reactant can be added to the reflux (407). Further, the reactant (420) can be any one of at least a portion of a circulating liquid (410) comprising the collected reactant or a portion of a newly added reactant component.

The flow (420) including the reactant may preferably have a concentration of the reactant (which acts as an entrainer) of 80 mass % or more, more preferably 90 mass % or more. When the reactant concentration is less than 80 mass %, the amount of the flow (420) to be supplied to the distillation step is liable to be increased so as to provide a desirable azeotropic composition, and the energy cost is liable to be increased due to an increase in the load to the reboiler.

Addition of Azeotropic Entrainer

The appropriateness of the addition of the liquid (420) to be supplied to the azeotropic distillation column (42) as an azeotropic entrainer, and the amount thereof to be added can be determined on the basis of the following standards (I) to (II).

(I) The advantage derived from the improved efficiency of the azeotropic distillation column (42) is greater than the disadvantage caused in the reactant recovery step (44).

The above-mentioned advantage refers to the economic effect that comes from the improvement in the separation performance of the azeotropic distillation column (42). Generally, in a distillation step in which a refluxing operation is carried out to reduce the concentration of the high boiling component in the column-top fraction of distillate, the energy required in the reboiler (43) for the azeotropic distillation column (42) is increased by the amount to be supplied to the distillation column as a reflux. However, as the composition of the column-top fraction of distillate (406) approaches the composition of an azeotropic composition with a minimum boiling point, as a result of the practice of the present invention, the predetermined separation performance can be attained with less reflux, and the energy required in the reboiler (43) for the azeotropic distillation column (42) can be reduced. Alternatively, the processing cost in the subsequent step can be reduced, because the amount of high-boiling component flowing from the top of the distillation column is decreased as a result of the reduction in the concentration of the high boiling component.

On the other hand, the above-mentioned disadvantage refers to the economic drawback of an increase in the amount to be processed in the reactant recovery step (44), because the amount of unreacted reactant to be circulated is increased by the amount of the same to be used as an entrainer, as a result of the practice of the present invention.

(II) In addition, constraints such as operating conditions, etc., should be satisfied. The operating conditions may generally be changed depending on the target compound to be produced or the equipment used. Accordingly, the operating conditions should be determined on the basis of the constraint, etc., of the target values for the flow rate (or flow volume), composition, etc., of any one of the liquid taken out from the top of the column or the liquid taken out from the bottom of the column, or of both of these liquids.

For example, in the specific process of Example 1 appearing hereinafter, the amount of heating steam to be used in an extraction agent recovery step in the post-process (which is the same as the extracting process described in Patent Document 1) was increased by 0.2 mass part per hour. On the other hand, the flow rate of acetic acid in the wasted water was decreased by 0.04 mass part per hour, because of the marked decrease in the concentration of acetic acid (high boiling component) at the top of the azeotropic distillation column. Therefore, the following in equation was satisfied in the case of Example 1.

The advantage of 0.04 mass part per hour of acetic acid (costs for wastewater treatment and the loss in acetic acid)

(about ten million yen per year)>the disadvantage of an increase of 0.2 mass part per hour of steam (about two million yen per year)

EXAMPLES

Hereinbelow, the present invention will be described in more detail while referring to specific Examples, but the present invention is never limited to these specific Examples.

Example 1

As Example 1, the present invention was practiced while referring to the allyl alcohol producing process of Patent Document 1.

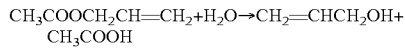

Hereinbelow, this example will be explained while referring to nation FIG. 5, which is a flow diagram for illustrating Example 1.

Referring to FIG. 5, a reactant (501) containing allyl acetate which has been produced through an allyl acetate synthesizing step is mixed with an allyl acetate reactant (502) which has been collected from an extraction column (55) appearing hereinafter, and the resultant mixture is supplied to a hydrolysis reactor (51).

A strongly acidic ion-exchange resin is used as a catalyst in the hydrolysis reaction (51), and the reaction is conducted at 0.6 MPa, at a temperature of 78° C. and a residence time of 50 minutes. A flow (505) in which a reaction product liquid (504) and a part (520) of the allyl acetate which has been collected from the extraction column (55) are mixed, is supplied to a distillation column (52). The distillation column (52) is operated at a pressure of 0.15 MPa, with the temperature at the top of the column being in the range of about 90° C. and the temperature at the bottom of the column being in the range of about 115° C. The liquid (506) taken out from the bottom of the column is a liquid mainly comprising acetic acid and water. This liquid (506) is returned to the allyl acetate synthesizing step and reused. The distillate fraction (507) from the column top is cooled to about 50° C. and supplied to a decanter (54). It is separated into two layers in the decanter (54), namely an oil layer having a high concentration of allyl acetate, and an aqueous layer having a low concentration of allyl acetate. A portion of the oil layer liquid is returned as a reflux (509) so as to improve the separation performance of the azeotropic distillation column (52), and the remaining oil layer liquid (510) is supplied to the extraction column (55).

On the other hand, the water layer (508) is supplied, together with the liquid (512) appearing hereinafter, to the allyl alcohol refining step. In the extraction column (55), under the conditions of a pressure of 0.110 MPa and a temperature of 40° C., a liquid (510) taken out from the top of the azeotropic distillation column (52) and a liquid (511) mainly comprising water are contacted with each other in a countercurrent flow, and the resultant flow is supplied at a proportion of (mass flow rate of liquid 510): (mass flow rate of liquid 511)=1:1.4; and allyl acetate (513) from which allyl alcohol has been removed is taken out from the top of the column, and an allyl alcohol aqueous solution (512) containing as small amount of allyl acetate is taken out from the bottom of the column. Incidentally, the water layer (508) and the allyl alcohol aqueous solution (512) are mixed, and in the next distillation column, after allyl acetate is removed from the resultant mixture, an azeotropic composition comprising allyl alcohol and water can be obtained from the column top, as a result of a distillation operation of the allyl alcohol aqueous solution. The allyl acetate (513) having a concentration of 97.3%, and having been collected in this manner is recycled as an azeotropic distillation entrainer (520) and a reactant (502) for the hydrolysis reactor (51).

At this point, the operating conditions of the hydrolysis reactor (51) and the decanter (54) were as described above, and an eight-hour test was carried out according to operation principles such that the flow rate of the column-bottom discharge (506) of the azeotropic distillation column (52) is 62.9 mass parts per hour, and the flow rate of the reflux (509) from the oil layer of the decanter (54) is 52.5 mass parts per hour, and these flow rates are kept constant. The average values of the composition and flow rate of each flow are shown in the following Table 1. At this time, the temperature in the column top of the distillation column (52) was 92.7° C., and amount of steam used in the reboiler (53) was 38.3 mass parts per hour. Further, the amount of allyl alcohol produced (i.e. the amount thereof to be transferred to the next process: (508)+(512)) was 12.4 mass parts per hour.

The flow rate and the composition data of each flow of Example 1 obtained at this time are shown in the following Table 1.

TABLE 1

| Flow No. | 501 | 502 | 503 | 504 | 505 | 506 | 507 | 508 | 509 | 510 | 511 | 512 | 513 | 520 |
| --- | --- | --- | --- | --- | --- | --- | --- | --- | --- | --- | --- | --- | --- | --- |
| Flow rate [mass part/hour] Mass concentration [%] | 90.0 | 10.0 | 100.0 | 100.0 | 103.0 | 62.9 | 88.5 | 4.0 | 52.5 | 36.0 | 50.0 | 73.0 | 13.0 | 3.0 |
| Allyl alcohol | 1.0 | 0.1 | 0.9 | 12.5 | 12.1 | 0.0 | 32.5 | 18.3 | 32.6 | 32.6 | 0.0 | 16.0 | 0.1 | 0.1 |
| Water | 42.9 | 2.5 | 38.8 | 35.2 | 34.3 | 41.5 | 16.9 | 75.6 | 17.0 | 17.0 | 99.9 | 76.4 | 2.5 | 2.5 |
| Allyl acetate | 28.6 | 97.3 | 35.4 | 15.5 | 17.9 | 0.0 | 50.5 | 6.0 | 50.4 | 50.4 | 0.0 | 7.5 | 97.3 | 97.3 |
| Acetic acid | 27.6 | 0.1 | 24.9 | 36.8 | 35.8 | 58.5 | 0.1 | 0.1 | 0.1 | 0.1 | 0.1 | 0.1 | 0.1 | 0.1 |

Example 2

Figure 6:
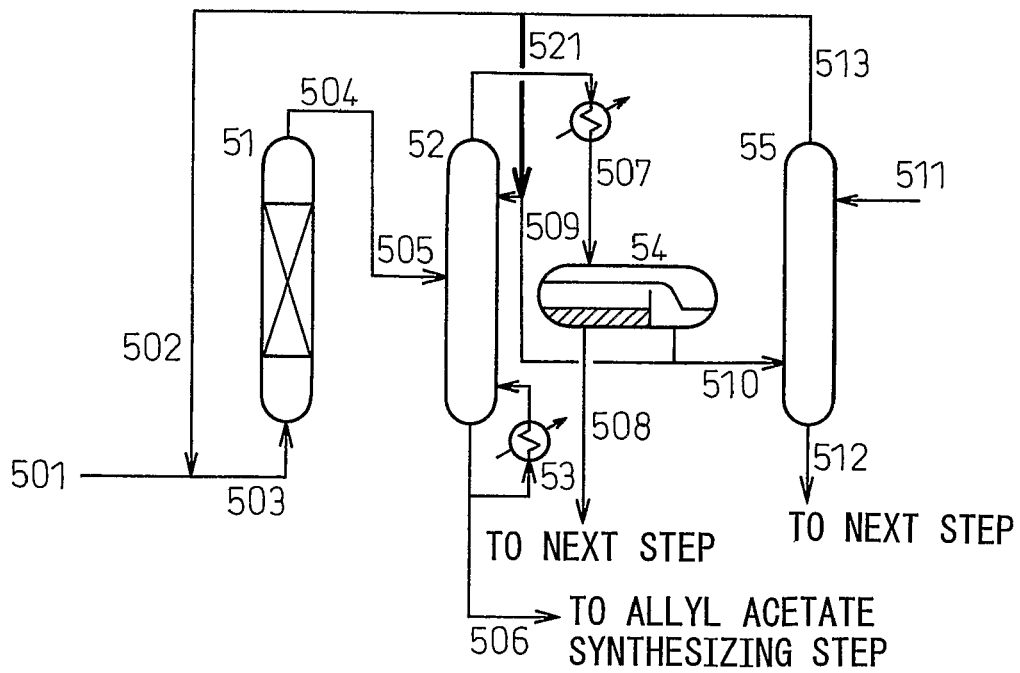
FIG. 6 is a flow diagram for illustrating the process flow of Example 2.

The flowchart (flow diagram) shown in FIG. 6 is provided for illustrating Example 2. (In the explanation of FIG. 6, the parts or portions corresponding to those shown in FIG. 5 are denoted by the same reference numerals as used in FIG. 5, and the explanations thereof are omitted (i.e., not repeated).

As shown in FIG. 6, an experiment was carried out under the same conditions as in Example 1 with respect to the operating conditions of the hydrolysis reactor (51) and the decanter (54) and the flow rate of the column-bottom discharge (506) of the azeotropic distillation column (52), except that allyl acetate collected from the extraction column, represented by the flow (521), was supplied to the reflux (509) of the azeotropic distillation column (52) and that the sum of the flow rates of the flows (509) and (521) was set to a value equal to or nearly equal to the corresponding value (i.e., 509) of Example 1. At the time, the temperature in the column top of the azeotropic column (52) was 92.2° C., and the amount of steam used in the reboiler (53) was 37.3 mass parts per hour. Further, the amount of allyl alcohol produced in this example (i.e., the amount thereof to be transferred to the next process: (508)+(512)) was 12.4 mass parts per hour.

The flow rate and the composition data of each flow of Example 2 obtained at this time are shown in the following Table 2.

TABLE 2

| Flow No. | 501 | 502 | 503 | 504 | 505 | 506 | 507 | 508 | 509 | 510 | 511 | 512 | 513 | 521 |
|---|---|---|---|---|---|---|---|---|---|---|---|---|---|---|
| Flow rate [mass part/hour] | 90.0 | 10.0 | 100.0 | 100.0 | 100.0 | 62.9 | 89.6 | 4.1 | 49.6 | 35.9 | 50.0 | 72.9 | 13.0 | 3.0 |
| Mass concentration [%] | | | | | | | | | | | | | | |
| Allyl alcohol | 1.0 | 0.1 | 0.9 | 12.5 | 12.5 | 0.0 | 31.9 | 18.4 | 32.6 | 32.6 | 0.0 | 16.0 | 0.1 | 0.1 |
| Water | 42.9 | 2.5 | 38.8 | 35.2 | 35.2 | 41.5 | 19.7 | 75.4 | 17.0 | 17.0 | 99.9 | 76.4 | 2.5 | 2.5 |
| Allyl acetate | 28.6 | 97.3 | 35.4 | 15.5 | 15.5 | 0.0 | 48.3 | 6.0 | 50.3 | 50.3 | 0.0 | 7.4 | 97.3 | 97.3 |
| Acetic acid | 27.6 | 0.1 | 24.9 | 36.8 | 36.8 | 58.5 | 0.1 | 0.1 | 0.1 | 0.1 | 0.1 | 0.1 | 0.1 | 0.1 |

Comparative Example 1

Figure 7:
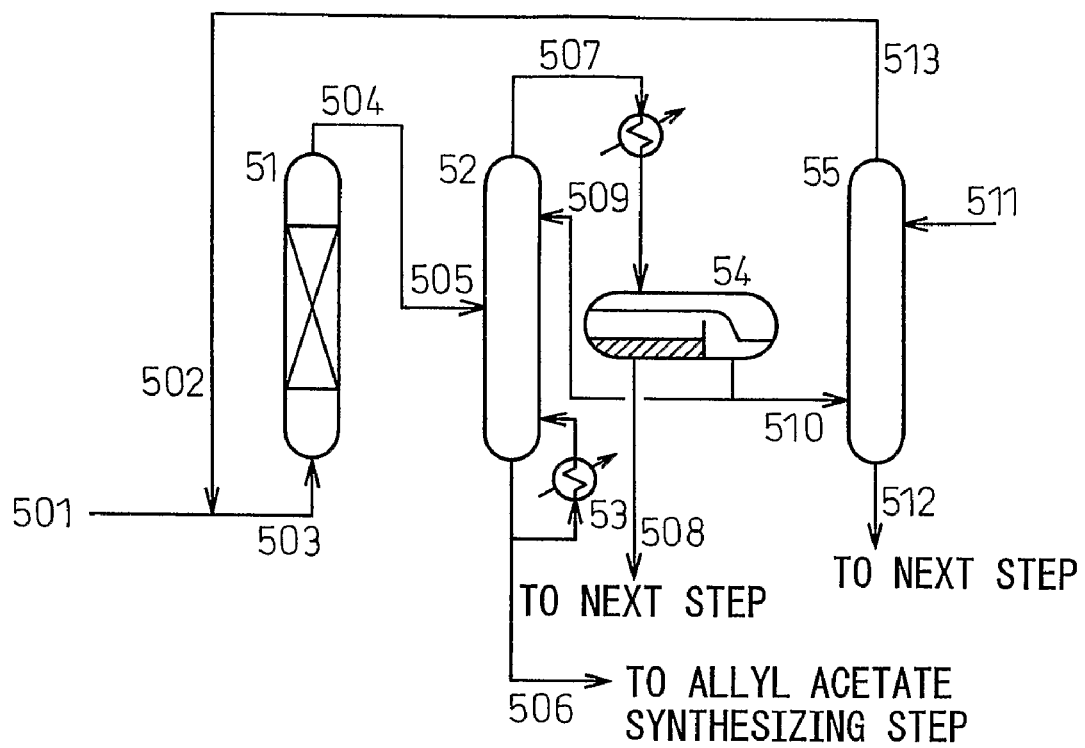
FIG. 7 is a flow diagram for illustrating the process flow of Comparative Example 1 and Comparative Example 2.

The flowchart (flow diagram) shown in FIG. 7 is provided for illustrating the Comparative Example 1. (In the explanation of FIG. 7, the parts or portions corresponding to those shown in FIG. 5 are denoted by the same reference numerals as used in FIG. 5, and the explanations thereof are omitted.)

As shown in FIG. 7, an experiment was carried out under the same conditions as Example 1 with respect to the operating conditions of the hydrolysis reactor (51) and the decanter (54) and the flow rate of (506), except that the flow rate of the reflux (509) was increased to 54.9 mass parts per hour to suppress the concentration of acetic acid in the column-top fraction of distillate, provided that a reactant is not added as an entrainer (so that the flow rate of the flow (520) in FIG. 5 was 0 (zero)). At the time, the temperature in the column top of the azeotropic column (52) was 93.2° C., and the amount of steam used in the reboiler (53) was 41.2 mass parts per hour. Further, the amount of allyl alcohol produced (the amount thereof to be transferred to the next process: (508)+(512)) was 12.4 mass parts per hour.

The flow rate and the composition data of each flow of Comparative Example 1 obtained at this time are shown in the following Table 3.

As described above, the amounts of allyl alcohol produced in Example 1, Example 2 and the Comparative Example 1 were almost equal to each other, but in Examples 1 and 2, it was possible to reduce the amount of steam used in the reboiler (53).

Example 3

An experiment was carried out under the same conditions as in Example 1 for 223 days, so that allyl acetate (such as flow (520), concentration: 97.3%) collected from the distillation column is supplied to the outlet (504) of the hydrolysis reactor (51), as an azeotropic entrainer. The amount of the product produced in this period was 100.0 mass parts per hour, on average.

The temperature in the column top of the azeotropic column (52) was 91.4° C., the temperature in the column bottom thereof was 116.9° C., and the pressure therein was 0.110 MPa. The pressure at the top of the extraction column (55) was 0.110 MPa. The amount of steam used in the reboiler (53) was 316 mass parts per hour on average, and the total amount of steam used in the allyl alcohol producing process (including the post treatment) was 356 mass parts per hour on average. Further, the recovery factor of the acetic acid from the column bottom of the azeotropic column (52) was 99.9%, based on the total amount of the acetic acid which had been supplied to the azeotropic column (52).

The flow rate and the composition data of each flow of Example 3 obtained at this time are shown in the following Table 4.

TABLE 3

| Flow No. | 501 | 502 | 503 | 504 | 505 | 506 | 507 | 508 | 509 | 510 | 511 | 512 | 513 |
|---|---|---|---|---|---|---|---|---|---|---|---|---|---|
| Flow rate [mass part/hour] | 90.0 | 10.0 | 100.0 | 100.0 | 100.0 | 63.0 | 89.6 | 2.4 | 54.9 | 34.7 | 48.6 | 73.3 | 10.0 |
| Mass concentration [%] | | | | | | | | | | | | | |
| Allyl alcohol | 1.0 | 0.1 | 0.9 | 12.5 | 12.5 | 0.0 | 34.5 | 19.5 | 34.5 | 34.5 | 0.0 | 16.3 | 0.1 |
| Water | 42.9 | 2.5 | 38.8 | 35.2 | 35.2 | 41.7 | 21.0 | 76.0 | 21.0 | 21.0 | 99.4 | 75.5 | 2.5 |
| Allyl acetate | 28.6 | 97.1 | 35.4 | 15.5 | 15.5 | 0.0 | 44.1 | 4.3 | 44.1 | 44.1 | 0.0 | 7.6 | 97.1 |
| Acetic acid | 27.6 | 0.3 | 24.9 | 36.8 | 36.8 | 58.3 | 0.4 | 0.3 | 0.4 | 0.4 | 0.6 | 0.5 | 0.3 |

TABLE 4

| FLOW No. | 501 | 502 | 503 | 504 | 505 | 507 | 508 | 509 | 510 | 511 | 513 | 520 |
|---|---|---|---|---|---|---|---|---|---|---|---|---|
| flow rate [mass part/hour] | 697 | 144 | 841 | 841 | 855 | 772 | 37 | 439 | 296 | 556 | 159 | 15 |
| Mass concentration [%] | | | | | | | | | | | | |
| Allyl alcohol | 0.2 | 0.3 | 0.2 | 12.1 | 11.9 | 31.7 | 17.2 | 32.4 | 32.4 | 0.1 | 0.3 | 0.2 |
| Water | 48.1 | 2.2 | 40.2 | 36.5 | 35.9 | 18.0 | 78.9 | 14.9 | 14.9 | 99.8 | 2.1 | 1.6 |
| Allyl acetate | 25.0 | 97.5 | 37.4 | 16.9 | 18.3 | 50.3 | 3.9 | 52.6 | 52.6 | 0.0 | 97.5 | 98.2 |
| acetic acid | 26.6 | 0.1 | 22.1 | 34.4 | 33.8 | 0.1 | 0.1 | 0.1 | 0.1 | 0.2 | 0.1 | 0.1 |

| operating conditions | upper portion temp. [° C.] | lower portion temp. [° C.] | pressure at upper portion [kPa] |
|---|---|---|---|
| 51 | 73.3 | | 551.3 |
| 52 | 91.4 | 116.9 | 110.2 |
| 54 | 46.8 | | |
| 55 | 29.9 | 44.6 | 110.2 |

In Table 4, the pressure values are denoted in terms of absolute pressure.

Amount of the product obtained: 100.0 mass parts

Unit consumption of steam in reboiler (53): 3.16 mass parts/mass parts of allyl alcohol Unit consumption of steam in distillation system: 3.49 mass parts/mass parts of allyl alcohol Recovery factor of acetic acid from azeotropic column (52): 99.9%

Comparative Example 2

An experiment was carried out under the same conditions as in Comparative Example 1 (so that the flow rate of the flow (520) in FIG. 5 was 0 (zero)) for 167 days. The amount of the product produced in this period was 108.8 mass parts per hour, on average.

The temperature in the column top of the azeotropic column (52) was 92.0° C., the temperature in the column bottom thereof was 117.4° C., and the pressure therein was 0.112 MPa. The pressure at the top of the extraction column (55) was 0.112 MPa. The amount of steam used in the reboiler (53) was 375 mass parts per hour on average, and the total amount of steam used in the allyl alcohol producing process (including the post treatment) was 464 mass parts per hour on average. Further, the recovery factor of the acetic acid from the column bottom of the azeotropic column (52) was 99.6%, based on the total amount of the acetic acid which had been supplied to the azeotropic column (52).

The flow rate and the composition data of each flow of Comparative Example 2 obtained at this time are shown in the following Table 5.

TABLE 5

| FLOW No. | 501 | 502 | 503 | 504 | 505 | 507 | 508 | 509 | 510 | 511 | 513 | 520 |
|---|---|---|---|---|---|---|---|---|---|---|---|---|
| flow rate [mass parts/hour] | 633 | 143 | 776 | 776 | 776 | 833 | 26 | 508 | 299 | 534 | 143 | 0 |
| Mass concentration [%] | | | | | | | | | | | | |
| allyl alcohol | 0.8 | 0.2 | 0.7 | 14.7 | 14.7 | 36.0 | 19.9 | 36.6 | 36.6 | 0.0 | 0.2 | 0.0 |
| water | 48.2 | 2.2 | 39.7 | 35.4 | 35.4 | 18.8 | 75.7 | 17.0 | 17.0 | 99.5 | 2.2 | 0.0 |
| allyl acetate | 29.6 | 97.3 | 42.1 | 17.9 | 17.9 | 44.9 | 4.2 | 46.2 | 46.2 | 0.0 | 97.3 | 0.0 |
| acetic acid | 21.4 | 0.3 | 17.5 | 32.0 | 32.0 | 0.2 | 0.2 | 0.3 | 0.3 | 0.4 | 0.3 | 0.0 |

| operating conditions | upper portion temp. [° C.] | lower portion temp. [° C.] | pressure at upper portion [kPa] |
|---|---|---|---|
| 51 | 77.5 | | 551.3 |
| 52 | 92.0 | 117.4 | 112.2 |
| 54 | 44.6 | | |
| 55 | 29.2 | 46.8 | 112.2 |

In Table 5, the pressure values are denoted in terms of absolute pressure.

Amount of the product obtained: 108.8 mass parts

Unit consumption of steam in reboiler (53): 3.44 mass parts/mass parts of allyl alcohol Unit consumption of steam in distillation system: 4.13 mass parts/mass parts of allyl alcohol Recovery factor of acetic acid from azeotropic column (52): 99.6%

The invention claimed is:

1. A process for producing allyl alcohol, comprising at least, a reaction step for hydrolyzing allyl acetate, an azeotropic distillation step for separating and refining allyl acetate and allyl alcohol, and an extraction step for recovering allyl acetate from a liquid taken out from a top of the azeotropic distillation step;
   wherein a portion of a liquid and/or gas, which has been recovered in the extraction step and comprises 90 mass % or more of allyl acetate which acts as an entrainer, is supplied directly to the azeotropic distillation step.

2. A process for producing allyl alcohol according to claim 1, wherein the azeotropic distillation step uses a plurality of distillation columns, and a portion of the liquid and/or gas, which has been recovered in the extraction step and comprises 90 mass % or more of allyl acetate which acts as an entrainer, is supplied directly to the first column to be used in the azeotropic distillation step.

* * * * *